United States Patent [19]
Smith et al.

[11] Patent Number: 5,282,571
[45] Date of Patent: Feb. 1, 1994

[54] PLASTIC VISOR CLIP

[75] Inventors: Gerald G. Smith, Orland Park; Robert T. Wicks, Chicago; Hari Matsuda, Evanston, all of Ill.

[73] Assignee: Gold Eagle Co., Chicago, Ill.

[21] Appl. No.: 2,651

[22] Filed: Jan. 11, 1993

[51] Int. Cl.$^5$ .............................................. A61L 9/12
[52] U.S. Cl. ............................................ 239/54; 239/34
[58] Field of Search ................ 239/34, 36, 54, 52, 239/59; 24/555, 545, 556, 562, 563; 296/97.5

[56] References Cited

U.S. PATENT DOCUMENTS

| | | | |
|---|---|---|---|
| 3,400,890 | 9/1968 | Gould | 239/54 X |
| 4,802,626 | 2/1989 | Forbes et al. | 239/36 |
| 4,874,129 | 10/1989 | DiSapio et al. | 239/36 |
| 4,940,272 | 7/1990 | Weick | 296/97.5 |
| 5,004,138 | 4/1991 | Gabas | 239/59 X |
| 5,113,554 | 5/1992 | Gallo et al. | 24/545 |
| 5,170,938 | 12/1992 | Dewing | 239/52 |

FOREIGN PATENT DOCUMENTS 2908527 9/1980 Fed. Rep. of Germany ........ 239/36

OTHER PUBLICATIONS

Publication from the International Flavors and Fragrances Company of Rosemont, Ill. and describing their product sold under the trademark POLYIFF, 4 pages.

Primary Examiner—Andres Kashnikow
Assistant Examiner—Lesley D. Morris
Attorney, Agent, or Firm—Gerstman & Ellis, Ltd.

[57] ABSTRACT

A plastic clip for automobile visors and the like. The clip comprises a plastic material impregnated with an aroma-creating material which is continuously released from the plastic material into the air for a period of weeks when mounted on the visor. The plastic material of the visor itself can be used to provide the clip action.

15 Claims, 1 Drawing Sheet

PLASTIC VISOR CLIP

BACKGROUND OF THE INVENTION

Automobiles (including trucks, recreational vehicles, vans and the like) are subject to a large variety of environments and uses so that, as they age, the familiar and pleasing "new car" aroma disappears, often being replaced with something less desirable. In the prior art, spray can deodorants and the like are sold to remove unpleasant automobile odors, and/or to add a pleasing aroma to the environment within the auto. Aromas are even applied to old car interiors which remind the user of a new car.

However, such aromas are, of course, short lasting as the automobile is used. Likewise, where a continuous release air freshener is applied to a car, there is no really good place to put it.

By this invention, an aroma-providing device is readily attachable at an out-of-the-way place of the automobile, while providing a decorative component to the car interior. Also the device is cheap and long lasting, providing a desired aroma to the car interior.

DESCRIPTION OF THE INVENTION

By this invention, a plastic clip is provided for automobile visors. The clip comprises means for attachment to an automobile visor, and also comprises a plastic material which is impregnated with an aroma-creating material which is continuously released from the plastic material into the air for a period of weeks, at least two or three weeks, and typically for periods of three months and more. The plastic clip is mounted on a visor of the automobile, where it may be a decorative asset, as well as providing the continuous release of the desired aroma.

Preferably, the plastic clip of this invention is made entirely of the desired plastic in a single piece, without added metal clips or the like. The plastic clip of this invention typically defines a central plastic body plus a pair of plastic side projections integrally connected with the body. The side projections are positioned to grip an automobile visor between them by spring action, generally by the natural spring action of the plastic. This causes retention of the clip on the automobile visor.

It may be desirable for the two side projections referred to above to each be of different size. For example, one of the side projections may define a central aperture which is of substantially the size and shape of the other of the side projections.

It is also typical for one of the side projections to connect to the central, plastic body with a single, continuous junction area, while the other side projection connects to the central, plastic body with a pair of spaced junction areas. The single, continuous junction area may be positioned between the spaced junction areas.

Thus, by such a construction, the visor clip of this invention may be thermoformed from a flat sheet of the plastic, with one of the side projections being cut out of an inner part of the other of the side projections during the thermoforming process. Alternatively, the visor clip may be injection molded.

Typically, the one side projection described above and the central plastic body substantially occupy a plane. The other side projection may have portions extending from the spaced junction areas in a direction which is out of the plane. Then, an outer portion of that other side projection may be bent to taper back toward the plane.

Thus a clip may be provided in which the side projections are pulled apart, and the automobile visor placed between them. Then, the clip is retained by spring action of its plastic against the visor, for long-term, controlled release of a desired aroma into the automobile interior.

The clip described above may also have integral plastic reinforcement means formed by the same process by which the plastic clip is formed, to hold the other side projection portion (as defined above) in its direction of extension out of the plane. This can be used to improve the spring-gripping action of the clip of this invention.

The clip of this invention may be made of essentially any plastic that is compatible with the controlled release of the desired aroma. Typically, the particular plastic, containing the aroma agent, may be manufactured by technology which is known to the industry, with such plastics being available under the trademark POLYIFF, from International Flavors and Fragrances Inc. of Rosemont, Ill. Typically complex mixtures of fragrance ingredients are dispersed in a plastic resin matrix as the matrix is molded into the clip of this invention. Thus, initially, the fragrance is uniformly dispersed throughout the entire plastic matrix.

Examples of plastics which can be used in this manner include high and low density polyethylene, polypropylene, poly (ethylene-vinyl acetate), resins that are compatible with poly-vinyl chloride, poly-vinyl chloride itself, and the like. The desired clip of this invention may be injection molded from powdered or pelleted resin having the fragrance mixed therein. As previously stated, it may also be thermoformed from a sheet of the fragrance-carrying plastic resin.

Any desired fragrance may be used. The industry has many potential fragrance ingredients that may be used in any desired practical concentration. Floral aromas may be used, or, if desired, a known aroma formulation which is reminiscent of new cars. Aromas which are stimulating, stress relieving, or romantic may be formulated into the plastic as desired.

DESCRIPTION OF SPECIFIC EMBODIMENTS

Figure 1:
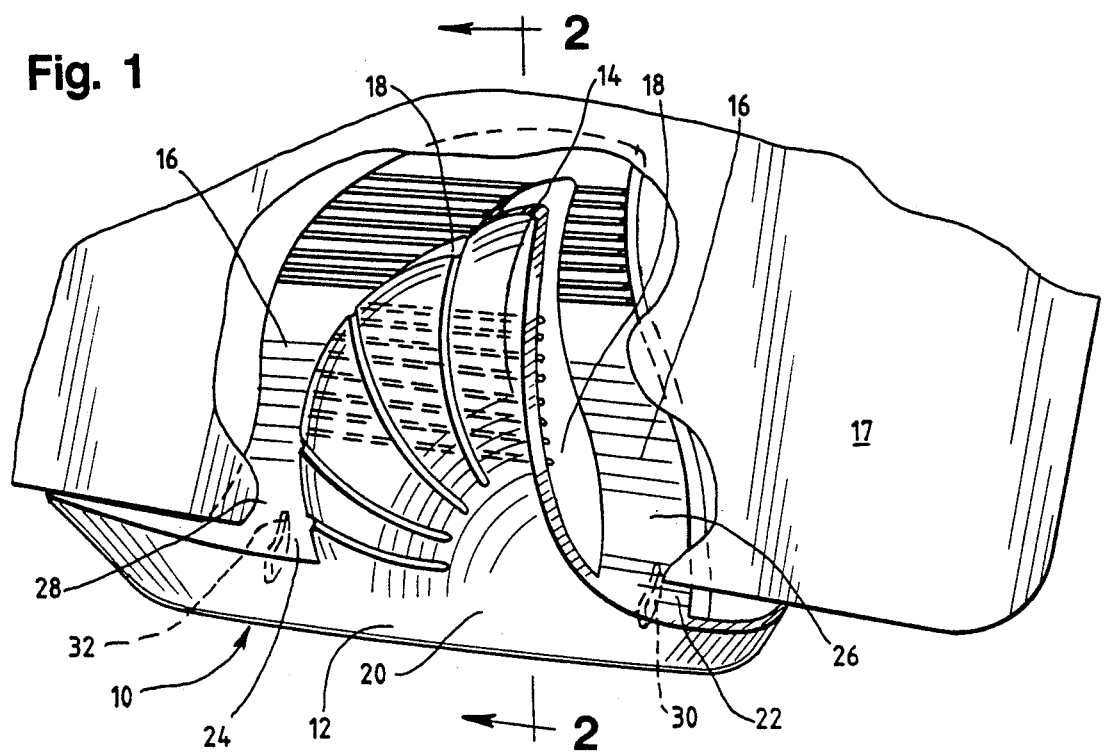
FIG. 1 is a perspective view of the plastic clip of this invention, carried on a windshield visor.

Referring to the drawings, a plastic clip 10 is shown, being made of a single, integral piece of plastic which is generally uniformly impregnated with an aroma-creating material that slowly leaches out into the air over a period of three months or more.

Clip 10 defines a central plastic body 12 plus a pair of plastic side projections: inner projection 14 and outer projection 16, each of which are integrally connected with plastic body 12. Side projections 14, 16 are positioned to grip an automobile visor 17 between them by spring action for retention of the clip, as shown.

Outer side projection 16 comprises a central aperture 18 which is substantially of the size and shape of the inner side projection 14.

By way of further description, inner side projection 14 connects to central plastic body 12 with a single, continuous junction area 20, while the outer side projection 16 connects to central plastic body 12 with a pair of spaced junction areas 22, 24. As shown, single, continuous junction area 20 is positioned between the spaced junction areas 22, 24.

Figure 2:
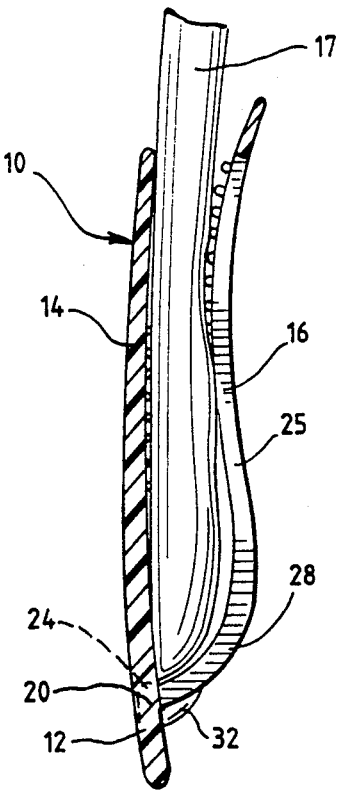
FIG. 2 is a sectional view taken along line 2—2 of FIG. 1.

As shown in FIG. 2, inner side projection 14 and central plastic body 12 substantially occupy a plane, while outer side projection 16 has portions 26, 28 extending from its spaced junction areas 22, 24 in a direction out of the above-described plane, as shown in FIG. 2. The outer portion 25 of projection 16 then bends back toward the plane of projection 14 to facilitate spring retention on a car windshield visor 17.

Also, integral plastic reinforcements, fins, or vanes 30, 32 hold the side projection portions 26, 28 in their direction of extension out of the plane. Thus, as the side projections 14, 16 are pulled apart and an automobile visor 17 inserted between them, reinforcement fins 30, 32 assist in providing a good spring resistance of a desired amount to magnify the spring action, for firm retention of the clip on the automobile visor, without of course being excessively strong so that the user has difficulty with it.

The clip of this invention may be of any stylized shape, the specific clip shown being in the stylized form of an eagle. Typical visor clips can be expected to release their desired aroma for approximately three months before replacement is needed.

The plastic clip of this invention can be used to clip onto other flat attachment sites than a visor, if desired, for example file folders, notebook covers, or the like.

Specifically, a plastic clip as shown in the drawings may be made of 20 to 40 percent by weight of polyethylene or polypropylene, plus 60 to 80 percent by weight of POLYIFF pellets which have been uniformly mixed into the plastic, and which carry the desired aroma-creating ingredient. The mixture is then injection molded into the desired shape.

The above has been offered for illustrative purposes only, and is not intended to limit the scope of the invention of this invention of this application, which is as defined in the claims below.

That which is claimed is:

1. A plastic clip for automobile visors, said clip comprising a unitary piece of plastic material which defines a central plastic body plus a pair of plastic side projections integrally connected with said body, said side projections being positioned to grip an automobile visor between them by spring action for retention of the clip on said automobile visor, said plastic material of the side projections and body being impregnated with an aroma-creating material to provide an aroma which is continuously released from said plastic material into the air for a period of weeks when mounted on a visor.

2. The plastic clip of claim 1 in which one of said side projections and the central plastic body substantially occupy a plane, and the other of said side projections have portions extending from its junction with the plastic body in a direction out of said plane.

3. The plastic clip of claim 2 in which integral plastic reinforcement means holds the other of said side projection portions in their direction of extension out of said plane.

4. The plastic clip of claim 1 in which said side projections are each of a different size.

5. The plastic clip of claim 4 in which one of said side projections comprises a central aperture which is of substantially the size and shape of the other of said projections.

6. The plastic clip of claim 4 in which one of said side projections connects to said central, plastic body with a single, continuous junction area while the other side projection connects to said central, plastic body with a pair of spaced junction areas, said single, continuous junction area being positioned between said spaced junction areas.

7. The plastic clip of claim 6 in which said one side projection and the central plastic body substantially occupy a plane, said other side projection having portions extending from said spaced junction areas in a direction out of said plane.

8. The plastic clip of claim 7 in which integral plastic reinforcement means holds the other side projection portions in their direction of extension out of said plane.

9. The plastic clip of claim 4 which is thermoformed from a flat, plastic sheet.

10. The plastic clip of claim 1 which is made substantially completely of said impregnated plastic material.

11. A plastic clip for automobile visors, said clip comprising means for attachment to an automobile visor, said clip also comprising a plastic material which is impregnated with an aroma-creating material to provide continuous release of aroma from said plastic material into the air for a period of weeks when mounted on a visor, said plastic clip defining a central plastic body plus a pair of plastic side projections integrally connected with said body, said side projections each being of a different size, and being positioned to grip an automobile visor between them by spring action, for retention of the clip on said automobile visor, an outer of said side projections comprising a central aperture which is substantially of the size and shape of the other of said projections and connecting to said central plastic body with a pair of spaced junction areas, an inner of said side projections connecting to said central, plastic body with a single, continuous junction area, the single, continuous junction area being positioned between said spaced junction areas.

12. The plastic clip of claim 10 in which inner side projection and the central plastic body substantially occupy a plane, the outer side projection having portions extending from the spaced junction areas in a direction out of said plane.

13. The plastic clip of claim 12 in which integral plastic reinforcement means holds the outer side projection portions in their direction of extension out of said plane.

14. The plastic clip of claim 13 which is thermoformed from a flat, plastic sheet.

15. The plastic clip of claim 13 in which substantially all of said plastic clip comprises said impregnated plastic material.

* * * * *